United States Patent
Arya

(12) United States Patent     (10) Patent No.: US 8,691,291 B1
Arya     (45) Date of Patent: Apr. 8, 2014

(54) SYSTEM AND METHOD FOR PATIENT PREPARATION

(75) Inventor: Vijay Arya, Old Brookeville, NY (US)

(73) Assignee: Vikalp, Inc., Old Brookeville, NY (US)

( * ) Notice: Subject to any disclaimer, the term of this patent is extended or adjusted under 35 U.S.C. 154(b) by 257 days.

(21) Appl. No.: 12/749,210

(22) Filed: Mar. 29, 2010

Related U.S. Application Data

(62) Division of application No. 12/101,601, filed on Apr. 11, 2008, now abandoned.

(51) Int. Cl.
    *A01N 59/08*     (2006.01)
    *A61K 33/14*     (2006.01)
    *A61K 33/42*     (2006.01)
    *A61K 33/00*     (2006.01)
    *A61P 1/10*     (2006.01)

(52) U.S. Cl.
    USPC ............ 424/680; 424/606; 424/722; 514/892

(58) Field of Classification Search
    USPC .......................... 424/680, 606, 722; 514/892
    See application file for complete search history.

(56) References Cited

U.S. PATENT DOCUMENTS

| | | | |
|---|---|---|---|
| 5,077,048 A | 12/1991 | Kimura et al. | |
| 6,132,767 A | 10/2000 | Borody et al. | |
| 6,520,384 B2 | 2/2003 | Mehta | |
| 6,669,059 B2 | 12/2003 | Mehta | |
| 6,688,497 B2 | 2/2004 | Mehta | |
| 7,332,184 B2 | 2/2008 | Vanner et al. | |

FOREIGN PATENT DOCUMENTS

CA     2443970 A1     11/2002

OTHER PUBLICATIONS

Group III "Complete colon Cleansing", Ulysses Press, Berkeley, CA.*
"Yoga point—Shankha Prakshalana or Dhouti (Cleansing Process from Hatha Yoga": http://www.yogapoint.com/info/shankha_praksha.htm.*
Internet Archive: Wayback machine: http://web.archive.org/web/*/http://www.yogapoint.com/shankha_praksha.htm.*
Salt retrieved from internet: http://wiki.answers.com/Q/How_many_grams_of_salt_in_one_teaspoon. Retrieved on Dec. 7, 2011.*
A colonoscopy for IBS: retrieved from internet: http://www.livestrong.com/article/177582-a-colonoscopy-for-ibs/. Retrieved on Mar. 6, 2013.*
Arya, et al., "Efficacy of Lukewarm Saline Water and Exercise (Shankh Prakshalana) as Colonoscopy Preparation—Pilot Study," date unknown, 1 p.
Arya, et al., "Efficacy of Lukewarm Saline Water and Excercise as Colonoscopy Preparation—A Randomized, Endoscopist Blinded Study," 2009, 1 p.

(Continued)

*Primary Examiner* — Ernst Arnold
*Assistant Examiner* — Hong Yu
(74) *Attorney, Agent, or Firm* — Blank Rome LLP

(57) ABSTRACT

A method for preparing the human bowel to undergo colonoscopy. A salt solution, preferable having a 0.9% w/v concentration of sodium chloride in water and warmed to 40 C. degrees, is utilized. A series of twisting and maneuvering exercises, such as those used in Yoga, is also performed. A predetermine quantity of the salt solution is consumed during predetermined intervals between the exercise steps, intending to clear and cleanse the colon so as to prepare it to undergo colonoscopy within about 3 to 24 hours after the completion of the preparation.

9 Claims, 7 Drawing Sheets

(56) References Cited

OTHER PUBLICATIONS

Konar, et al., Cardiovascular Responses to Head-Down-Body-Up Postural Excercise (Sarvangasana), Indian Journal of Physiology and Pharmacology, 2000, vol. 44, No. 4, pp. 392-400, New Delhi, India.
Occhipinti, et al., "How to Choose the Best Preparation for Colonoscopy," Nature Reviews: Gastroenterology & Hepatology, May 2009, pp. 279-286, vol. 6, Nature Publishing Group, New York, NY, USA.
Hawes, et al., "Consensus Document on Bowel Preparation for Colonoscopy," Gastronintestinal Endoscopy, 2006, pp. 894-909, vol. 63, No. 7, Elsevier, Maryland Heights, MO, USA.
Winawar, et al., "Prevention of Colorectal Cancer by Colonoscopic Polypectomy," The New England Journal of Medicine, Dec. 1993, pp. 1-8, vol. 329, No. 27, Waltham, MA, USA.
Belsey, et al., "Systematic Review: Oral Bowel Preparation for Colonoscopy," Alimentary Pharmacology & Therapeutics, 2006, pp. 373-384, vol. 25, Blackwell Publishing Ltd., Wiley-Blackwell, Malden, MA, USA.
Dipalma, et al., "Clinical Trial: An Efficacy Evaluation of Reduced Bisacodyl Given as Part of a Polyethylene Glycol Electrolyte Solution Preparation Prior to Colonoscopy," Alimentary Pharmacology & Therapeutics, 2007, pp. 1113-1119, vol. 26, Wiley-Blackwell, Malden, MA, USA.
Cohen, et al., "Prospective, Randomized, Endoscopic-Blinded Trial Comparing Precolonoscopy Bowel Cleansing Methods," Disesases of the Colon and Rectum, Jul. 1994, pp. 689-696, vol. 37, No. 7, Springer, New York, NY, USA.
Kolts, et al., "A Comparison of the Effectiveness and Patient Tolerance of Oral Sodium Phosphate, Castor Oil, and Standard Electrolyte Lavage for Colonoscopy or Sigmoidoscopy Preparation," The American Journal of Gastroenterology, 1993, 1218-1223, vol. 88, No. 8, New York, NY, USA.
Bucher, et al., "Randomized Clinical Trial of Mechnical Bowel Preparation Versus No Preparation Before Elective Left-Sided Colorectal Surgery," British Journal of Surgery, 2005, pp. 409-414, vol. 92, John Wiley & Sons Ltd., Malden, MA, USA.
Markowitz, et al., "Acute Phosphate Nephropathy following Oral Sodium Phosphate Bowel Purgative: An Underrecognized Cause of Chronic Renal Failure," The American Society of Nephrology, 2005, pp. 3389-3396, vol. 16., Washington, DC, USA.
Barnes, et al., "Complementary and Alternative Medicine Use Among Adults and Children: United States, 2007," National Health Statistics Reports, Dec. 2008, pp. 1-24, No. 12, Centers for Disease Control and Prevention, Atlanta, GA, USA.
Barnes, et al., "Complementary and Alternative Medicine Use Among Adults: United States, 2002," Advance Data from Vital and Health Statistics, May 2004, pp. 1-20, No. 343, Centers for Diseas Control and Prevention, Atlanta, GA, USA.
Lin, et al., "State of Complementary and Alternative Medicine in Cardiovascular, Lung, and Blood Research: Executive Summary of a Workshop," Circulation, Journal of the American Heart Association, 2001, pp. 2038-2041, vol. 103, American Heart Association, Dallas, TX, USA.
Kothari, et al., "Studies on a Yogi During an Eight-Day Confinement in a Sealed Underground Pit," Indian Journal of Medical Research, 1973, pp. 1645-1650, vol. 61, No. 11, New Delhi, India.
Gopal, et al., "The Effect of Yogasanas on Muscular Tone and Cardio-Respiratory Adjustments," The Indian Journal of Medical Sciences, date unknown, pp. 438-443, Mumbai, India.
Galantino, et al., "The Impact of Modified Hatha Yoga on Chronic Low Back Pain: a Pilot Study," Alternative Therapies in Health and Medicine, Mar./Apr. 2004, pp. 56-59, vol. 10, No. 2, InnoVision Health Media, Boulder, CO, USA.
Walton, et al., "Review of Controlled Research on the Transcendental Meditation Program and Cardiovascular Disease: Risk Factors, Morbidity, and Mortality," NIH Public Access, 2004, pp. 1-7, National Institutes of Health, Bethesda, MD, USA.
Yogendra, et al., "Beneficial Effects of Yoga Lifestyle on Reversibility of Ischaemic Heart Disease: Caring Heart Project of International Board of Yoga," Journal of the Association of Physicians in India, Apr. 2004, pp. 283-289, vol. 52, Mumbai, India.
Parra-Blanco, et al., "The Timing of Bowel Preparation Before Colonoscopy Determines the Quality of Cleansing, and is a Significant Factor Contributing to the Detection of Flat Lesions: A Randomized Study," World of Gastroenterology, Oct. 2006, pp. 6161-6166, vol. 12., No. 38, The WJG Press, Beijing, China.
Sanaka, et al., "Afternoon Colonoscopies Have Higher Failure Rates than Morning Colonoscopies," American Journal of Gastroenterology, 2006, pp. 2726-2730, Wiley- Blackwell Publishing, Hoboken, NJ, USA.
Hewitt, et al., "Whole-Gut Irrigation in Preparation for Large-Bowel Surgery," The Lancet, Aug. 1973, pp. 337-340, New York, NY, USA.
Levy, et al., "Saline Lavage: A Rapid, Effective, and Acceptable Method for Cleansing the Gastrointestinal Tract," Gastroenterology, Feb. 1976, pp. 157-161, vol. 70, No. 2, American Gastroenterological Association, Bethesda, MD, USA.
Postuma, "Whole Bowel Irrigation in Pediatric Patients," Journal of Pediatric Surgery, Aug. 1982, pp. 350-352, vol. 17, No. 4, Elsevier, Maryland Heights, MO, USA.
Chattopadhyay, et al., "A Prospective Comparison of Two Regimes of Bowel Preparation for Pediatric Colorectal Procedures: Normal Saline with Added Potassium vs. Polyethylene Glycol," Pediatric Surgery International, Jan. 2004, pp. 127-129, issue 20, Springer, New York, NY, USA.
Davis, et al., "Development of a Lavage Solution Associated with Minimal Water and Electrolyte Absorption or Secretion," Gastroenterology, 1980, pp. 991-995, issue 78, American Gastroenterological Association, Bethesda, MD, USA.
Barrett, "New Ways of Thinking About (and Teaching About) Intestinal Epithelial Function," Advances in Physiology Education, 2008, pp. 25-34, issue 32, American Physiological Society, Bethesday, MD, USA.
Fordtran, et al., "The Mechanisms of Sodium Absorption in the Human Small Intestine," The Journal of Clinical Investigation, 1968, pp. 884-900, vol. 47, Ann Arbor, MI, USA.
Sandle, "Salt and Water Absorption in the Human Colon: A Modern Appraisal," Gut, 1998, pp. 294-299, vol. 43, BMJ Group, London, UK.
McHugh, et al., "Calories and Gastric Emptying: A Regulatory Capacity with Implications for Feeding," American Physiological Society, 1979, pp. 254-260, Bethesda, MD, USA.
Hunt, et al., "The Influence of Volume on Gastric Emptying," Journal of Physiology, 1954, pp. 459-474, vol. 126, Wiley-Blackwell, Malden, MA, USA.
Hunt, et al., "The Volume and Energy Content of Meals as Determinants of Gastric Emptying," Journal of Physiology, 1975, pp. 209-225, vol. 245, Wiley-Blackwell, Malden, MA, USA.
Ouazzani, "Thermoreceptors in the Digestive Tract and Their Role," Journal of the Autonomic Nervous System, 1984, pp. 246-254, vol. 10, Elsevier Science Publishers B.V., Maryland Heights, MO, USA.
Sun, et al., "Effect of Meal Temperature on Gastric Emptying of Liquids in Man," Gut, 1988, pp. 302-305, vol. 29, BMJ Group, London, UK.
Bateman, "Effects of Meal Temperature and Volume on the Emptying of Liquid From the Human Stomach," Journal of Physiology, 1982, pp. 461-467, vol. 331, Wiley-Blackwell, Malden, MA.
McArthur, "Gastric Acid Secretion, Gastrin Release, and Gastric Emptying in Humans as Affected by Liquid Meal Temperature," American Journal of Clinical Nutrition, 1989, pp. 51-54, vol. 49, American Society for Clinical Nutrition, Bethesda, MD, USA.
Burn-Murdoch, et al., "Does Lying on the Right Side Increase the Rate of Gastric Emptying?" Journal of Physiology, 1980, pp. 395-398, vol. 302, the Physiological Society, London, UK.
Anvari, et al., "Effects of Posture on Gastric Emptying of Nonnutrient Liquids and Antropyloroduodenal Motility," The American Physiological Society, 1995, pp. 868-871, Bethesda, MD, USA.
Moore, et al., "Effect of Body Posture on Radionuclide Measurements of Gastric Emptying," Digestive Diseases and Sciences, Dec. 1988, pp. 1592-1595, vol. 33, No. 12, Plenum Publishing Corporation, New York, NY, USA.

(56) References Cited

OTHER PUBLICATIONS

Amidon, et al., "Effects of Gravity on Gastric Emptying, Intestinal Transit, and Drug Absorption," Journal of Clinical Pharmacology, 1991, pp. 968-973, vol. 31, Sage Publications, Newbury Park, CA, USA.

Rao, et al., "Effects of Fat and Carbohydrate Meals on Colonic Motor Response," Gut, 2000, pp. 205-211, vol. 46, BMJ Group, London, UK.

Lin, et al., "Effect of Meal Volume on Gastric Emptying," Journal of Gastrointestinal Motility, Sep. 1992, pp. 157-163, vol. 4, No. 3, Wiley-Blackwell, Malden, MA, USA.

Hunt, et al., "The Pattern of Emptying of the Human Stomach," Journal of Physiology, 1951, pp. 157-168, vol. 113, Wiley-Blackwell, Malden, MA, USA.

Dapoigny, et al., "Effects of Physical Exercise on Colonic Motor Activity," The American Physiologal Society, 1991, pp. 646-652, Bethesda, MD, USA.

Medeiros, et al., "Is Colonic Electrical Activity a Similar Phenomena to Small-Bowel Electrical Activity?" Diseases of the Colon and Rectum, Jan. 1997, pp. 93-99, Springer, New York, NY, USA.

Rao, et al., "Effects of Acute Graded Exercise on Human Colonic Motility," American Journal of Physiology—Gastrointestinal and Liver Physiology, 1999, pp. 1221-1226, vol. 276, The American Physiological Society, Bethesda, MD, USA.

Kim, et al., "Effectiveness of Walking Exercise as a Bowel Preparation for Colonoscopy: A Randomized Controlled Trial," American Journal of Gastroenterology, 2005, pp. 1964-1969, Wiley-Blackwell, Malden, MA, USA.

Wolsko, "Use of Mind-Body Medical Therapies," Journal of General Internal Medicine, 2004, pp. 43-50, vol. 19, Springer, New York, NY, USA.

Tansy, "Experimental and Clinical Aspects of Gastrocolic Reflexes," Digestive Diseases, Jun. 1973, pp. 521-531, vol. 18, No. 5, S. Karger AG, Basel, Switzerland.

Author Unknown, "Yoga Simplified, Shankh Prakshalan," Gandhi Gyan Mandir Yoga Kendra, accessed on Jul. 14, 2008, 6 pp., at http://www.yogasimplified.com/yogasimplified/chapter9.htm.

Author Unkown, Shankha Prakshalana or Dhouti (Cleaning Process from Hatha Yoga), Yoga Point, accessed on Jul. 14, 2008, 6 pp., at http://www.yogapoint.com/info/shankha_praksha.htm.

Hunt, et al., "The Osmotic Effects of Some Simple Molecules and Ions on Gastric Emptying," The Journal of Physiology, 1960, pp. 254-269, vol. 154, The Physiological Society, Oxford, England.

Carter, et al., "Fatal Salt Poisoning Due to Gastric Lavage with Hypertonic Saline," The Medical Journal of Australia, 1971, pp. 539-541, The Australian Medical Association, Kingston, Australia.

Arya, et al. "Yoga and Bolus Lukewarm Saline as Colonoscopy Preparation: A Randomized Study," American Journal of Gastroenterology (submitted), 2010, pp. 1-30, New York, NY, USA.

Arya, et al., "Yoga Based Rapid Colonoscopy Preparation: A Randomized Study," 2010, 30 pp.

Author Unknown, "Shankh Prakshalana," date of publication is unknown, but is prior to Jun. 20, 2012, pp. 24-31.

Shankha Prakshalana or Dhouti (Cleaning Process from Hatha Yoga), Yoga Point, www.yogapoint.com/info/shankha_praksha.htm, Nov. 15, 2006.

V. Arya et al., "Rapid Colonoscopy Preparation Using Bolus Lukewarn Saline Combined with Sequential Posture Changes: A Randomized Controlled Trial," Mar. 2, 2013, 1 page.

Arya et al., "Rapid Colonoscopy Preparation Using Bolus Lukewarm Saline Combined with Sequential Posture Changes: A Randomized Controlled Trial," Dig. Dis. Sci., Mar. 2, 2013, 11 pages.

Belsey, "Meditations on Bowel Preps," Dig. Dis. Sci., vol. 58, Jun. 29, 2013, 2 pages.

* cited by examiner

SYSTEM AND METHOD FOR PATIENT PREPARATION

CROSS-REFERENCE TO RELATED APPLICATION

The present application is a divisional of and claims the benefit of U.S. patent application Ser. No. 12/101,601, filed Apr. 11, 2008, the entire disclosure of which is incorporated by reference herein.

BACKGROUND OF THE INVENTION

1. Field of Invention

The present invention is generally related to processes for preparing patients to undergo colonoscopic, endoscopic, or sigmoidoscopic examination, and for treatment. In particular, the present invention relates to the administration to a patient in need of such preparation a salt solution and instructions regarding performing certain maneuvers or exercises, including those known as Shankha Prakshalana, with the intention of cleansing the human bowel in preparation for examination and/or relating to treatment.

2. Description of the Related Art

Colon cancer is cancer of the large intestine (colon), the lower part of the human digestive system. Rectal cancer is cancer of the last six inches of the colon. Together, they are often referred to as colorectal cancers. About 112,000 people are diagnosed with colon cancer annually, and about 41,000 new cases of rectal cancer are diagnosed each year, according to the American Cancer Society.

Colon cancer incidence is not much different between males and females, however colon cancer is slightly more prevalent in women compared to men (ratio of 1.2:1). Rectal cancer is more common in males (ratio of 1.7:1). Colon cancer is more common among elderly persons compared to younger persons. The risk of developing colon cancer begins to increase from the age of 40 and goes up with every passing year. The median age of presentation of colon cancer varies according to the country. In the United States the median age at presentation is 72 years. Colon cancer is more common in African Americans compared to the Caucasian population in the United States. The incidence of colon cancer has been on the increase in African Americans since 1973 and the incidence in this ethnic group has gone up by about 30 percent during the last 3 decades. Incidence of colorectal cancer varies widely from country to country. Countries which are more industrialized like the United States, Canada, UK, Western Europe, and Australia, have a much higher incidence of colorectal cancer compared to less industrialized parts of the world, like Asia, Africa, and South America.

Most cases of colon cancer begin as small, noncancerous (benign) clumps of cells called adenomatous polyps. Over time some of these polyps become colon cancers. Polyps may be small and produce few, if any, symptoms. Regular screening tests can help prevent colon cancer by identifying polyps before they become cancerous. If signs and symptoms of colon cancer do appear, they may include changes in bowel habits, blood in the stool, persistent cramping, gas or abdominal pain. In that event, contemporary medical practice is that the patient undergo colonoscopic examination.

An "endoscopy" is a minimally invasive diagnostic medical procedure that is used to assess the interior surfaces of an organ by inserting a tube into the body. The instrument may have a rigid or flexible tube, and it not only provides an image for visual inspection and photography, but it also enables taking biopsies and retrieval of foreign objects.

A "colonoscopy" is a type of endoscopic examination of the large colon and the distal part of the small bowel using a CCD camera or a fiber optic camera on a flexible tube passed through the anus. It may provide a visual diagnosis (e.g. ulceration, polyps) and grants the opportunity for biopsy or removal of suspected lesions. A "sigmoidoscopy" is a type of colonoscopy that is the minimally invasive medical examination of the large intestine from the rectum through the last part of the colon.

A colonoscopy enables a physician to examine the interior of the entire large intestine, from the lowest part, the rectum, all the way up through the colon to the lower end of the small intestine. The procedure is used to diagnose the causes of unexplained changes in bowel habits. It is also used to look for early signs of cancer in the colon and rectum. Colonoscopy enables the physician to see inflamed tissue, abnormal growths, ulcers, bleeding, and muscle spasms. If anything unusual is in a colon, like a polyp or inflamed tissue, is found, the physician can remove a piece of it using tiny instruments passed through the scope, and then send it for a biopsy examination.

In preparing to undergo a colonoscopic examination, the colon must be free of solid matter for the test to be performed properly. Generally speaking, for one to three days, the patient is required to follow a low fiber or clear fluid-only diet. Examples of clear fluids are apple juice, bouillon, artificially flavored lemon-lime soda or sports drink, and of course water. It is very important that the patient remains hydrated.

Use of solutions to cleanse and irrigate (a.k.a. "bowel preps") are well known in the prior art. U.S. Pat. No. 6,132,767 provides a history of colonic evacuants, their problems, and various solutions that others have achieved. Currently, various methods are employed to clear and cleanse the bowel in preparation for the colonoscopy. Often, a liquid preparation designed to stimulate bowel movements is given by mouth, which may cause bloating. Other laxative preparations, such as castor oil, may also be used. Additional approaches include special diets or the use of enemas. There are three broad categories, based on pharmacological mechanism of action, of bowel preparations commonly prescribed by physicians: (1) isotonic salt solutions, (2) phosphate or magnesium based solutions, and (3) polyethylene glycol (PEG) based preps.

Historically, bowel prep products required patients to ingest isotonic saline. More recently, the day before the colonoscopy, the patient is either given an osmotic laxative preparation (such as Bisacodyl, phospho soda, sodium picosulfate, or sodium phosphate and/or magnesium citrate) and large quantities of fluid or whole bowel irrigation is performed using a solution of polyethylene glycol (PEG) and electrolytes (e.g. GoLytely, NuLytely). In addition, patients are advised to take additional stool softeners and other medications to assist such as sennakot, docusate sodium, and psyllium based products.

U.S. Pat. No. 6,688,497 teaches a method for preparing a pH balanced saline solution and using the saline solution for rinsing a nasal passage, but does not discuss combining with exercise or treating the bowels. U.S. Pat. No. 5,077,048 discloses using a sodium chloride solution for irrigating the bowels, but does not discuss combining with exercise nor does it teach an isotonic concentration. U.S. Pat. No. 7,332,184 discloses using a sodium chloride solution for irrigating the colon, but does not discuss combining with exercise not does it teach an isotonic concentration.

Thus, while the prior art contains some patents that teach the use of sodium chloride to irrigate body cavities, and specifically the bowel and colon, none of these references teach preparation techniques involving use of exercise or yoga in combination with irrigation solutions to enhance bowel preparation efficacy. Likewise, most of the references also do not indicate the osmolarity or temperature of the specific disclosed solution.

Adequate colon preparation is essential for successful visualization of the colon, and essential for the detection of suspicious lesions. However, studies using large databases of patients reveal that up to 23% of all colonoscopies have suboptimal bowel preparation resulting in longer procedural times, poor intubation rates, and decreased polyp detection. Inadequate preparation may lead to incomplete visualization of the colon, resulting in shortened screening intervals due to concerns about missed lesions.

In addition, the use of PEG based bowel preparations are associated with the following adverse side effects: bloating; nausea; rectal irritation; stomach fullness or cramps; vomiting, and to a lesser extent, allergic reactions (e.g. rash, hives, itching, etc.). Phosphate-based preparations are commonly associated with bloating, nausea, abdominal pain, and vomiting, and to a lesser extent, cardiac arrhythmias, seizures, and renal failure.

Given these side-effects, coupled with the volume and taste of the fluid in the preparations, patients often complain that consuming the preparation is worse than undergoing the colonoscopy. Thus, poor compliance with proper bowel cleansing is often a significant issue with patients presenting for colonoscopy. In fact, inadequate bowel preparation is one of the most common reasons polyps are missed during colonoscopy. Lastly, another restrictive requirement on all contemporary agents used to prepare the bowel for colonoscopy is that those agents must be used or performed on the night before the examination, or at least 12 to 24 hours before.

The medical and overall health benefits of exercise and physical activity have been well documented. The merits of exercise range from preventing chronic health conditions to boosting confidence and self-esteem. Exercise is known to stimulate various brain chemicals, lowers cholesterol and plaque build up in the arteries, improves reuptake of sugar, reduces weight, and promotes better sleep. More importantly, exercise is known to prevent the occurrence and recurrence of colorectal cancer.

Yoga is a group of ancient spiritual practices originating in India. In the medical context, yoga is a simple, non-athletic set of movements and stretches that improve health. Shankha prakshalana is a specific subgroup of Yoga which includes a process to clean the intestinal tract by removing the impurities with salty water and set of exercise positions. For example, the website entitled Yoga Vidya Dham—Yoga Point teaches the performance of the Shankha Prakshalana exercises, and discloses the use of a solution, to clean and cleanse the alimentary tract. Similarly, the website entitled Gandhi Gyan Mandir Yoga Kendra discloses the use of Shankha Prakshalana technique along with a salt solution of 1%. However, neither of those references disclose an isotonic concentration, nor do they discuss the use of the solution and technique for the specific purpose of preparing a patient for colonoscopy, or that the outcome of the Shankha Prakshalana techniques achieves the efficacy necessary for a colonoscopy. Moreover, both websites state that the procedures should be done under direct and strict supervision.

While there is no one uniform approach to Shankha Prakshalana, the ingredients typically used in the solution are limited to salt, water, and lemon juice. Given the simple and natural characteristics of the ingredients, reports of severe adverse reactions in performing Shankha Prakshalana are uncommon. However, nausea, dizziness, bloating, diaphoresis, salt and water retention, general body edema, have been associated with Shankha Prakshalana. Moreover, patients who suffer from hypertension, salt sensitiveness, arthritis, and who are pregnant are contraindicated from performing Shankha Prakshalana.

Given the compliance problems noted above and the need for effective and safe alternative to existing bowel preparation techniques, a better patient preparation method is needed, and one that involves irrigating, clearing and/or cleansing the colon of a patient to such a degree that the patient is available to undergo successful colonoscopy, and one that utilizes natural ingredients and that has a minimal adverse reaction profile, so as to encourage compliance among patients. Lastly, what is needed is an inexpensive and relatively fast method to achieve the cleansing and clearing such that the colonoscopy procedure could be performed on the same day as the preparation procedure.

SUMMARY AND OBJECTS OF THE INVENTION

Accordingly, it is a principal object of the present invention to provide a method for cleansing and clearing a patient's bowel.

It is another object of the present invention to provide a method that accomplished the cleansing and clearing of a patient's bowel so as to render the patient prepared and suited to undergo colonoscopy by endoscope within 24 hours of performing the method. In particular, an average patient, not suffering from constipation, may achieve the requisite cleansing and clearing within 2 to 3 hours, if that patient eats only a light meal the night before examination, and wakes up about 5 AM on the day of the examination and performs the claimed process, then bowel movements will begin within 30 to 45 minutes of commencing process. Hence, it is another an object of the present invention to provide a same-day, faster alternative to cleansing and clearing a colon in preparation for colonoscopy compared to the current agents in the prior art.

It is still another object of the present invention to provide a method that cleanses and clears a patient's bowels and prepares it for colonoscopy that utilizes alternative, natural ingredients without precipitating the side effects typically associated with conventional prescription and non-prescription commercially available bowel preparation medical kits.

It is another object of the present invention to conduct examinations of a patient's bowel after the patient has completed the sequence of steps of administering a salt solution followed by prescribed exercises according to the present invention.

It is another object of the present invention to provide a novel approach to preparing the bowel for colonoscopy, which is relatively quick in that it may be performed on the day of and just a few hours prior to the exam, and which is relatively inexpensive as it uses commonly available products.

Briefly described, those and other objects and features of the present invention are accomplished, as embodied and fully described herein, by a method of preparing a patient's colon for a colonoscopic examination by endoscope or other means, which involves administering to said patient a treatment regimen, the treatment regiment including an oral cleansing solution and a sequential series of exercises. In particular, the treatment regimen includes administering to the patient a first predetermined quantity of a salt solution at a first predetermined time period; and performing by the patient a first exercise at a second predetermined time period that is different than the first time period, wherein the administering and performing steps are intending to effectively prepare a colon of the patient to undergo the colonoscopic examination. The method further includes the step of performing the colonoscopic examination of the patient within about 24 hours of the first and second time periods. Preferably, the solution contains a concentration made from 15 to 20 grams of sodium chloride per 2 liters of water, and most preferably the solution contains from 18 grams of sodium chloride per 2 liters of water. The solution should be maintained at about 4° C.

The objects and features of the present invention are also accomplished, as embodied and fully described herein, by a kit for colonic cleansing prior to colonoscopic examination, which contains a package, such as a satchet, comprising sodium chloride and a flavorant for mixing with a diluent; and an instruction device, the instruction device containing instructions for performing a sequential series of exercises. The instruction device may be a computer-readable medium device containing instructions thereon for displaying images and audio on a computing device for the patient to view and follow in order to perform the steps in the correct sequence.

With those and other objects, features, and advantages of the invention that may become hereinafter apparent, the nature of the invention may be more clearly understood by reference to the following detailed description of the invention, the appended claims, and to the several drawings attached herein.

BRIEF DESCRIPTION OF THE DRAWINGS

Many aspects of the invention can be better understood with reference to the following drawings.

DETAILED DESCRIPTION OF THE PREFERRED EMBODIMENT

Figure 1:
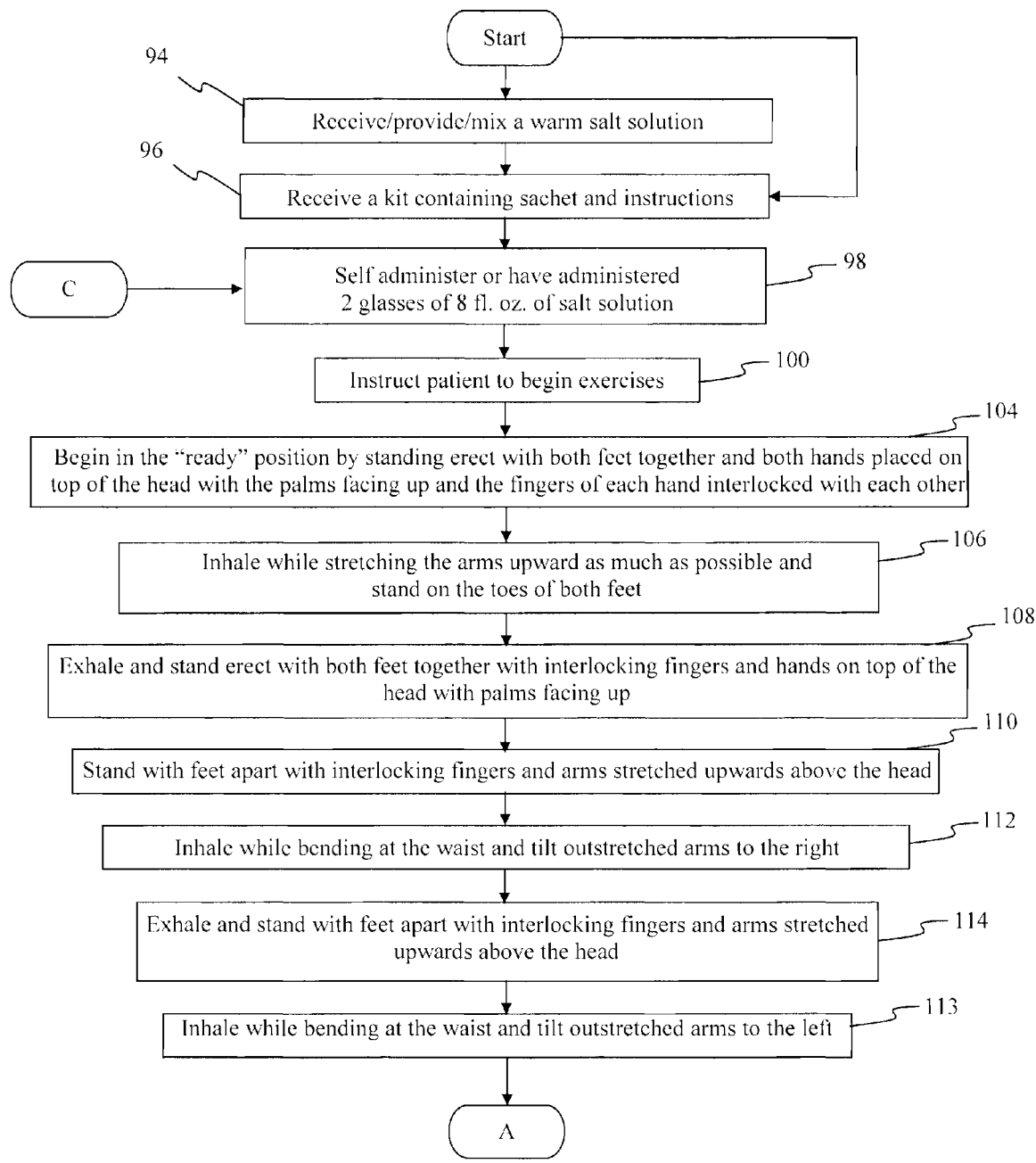
FIGS. 1-1, 1-2, and 1-3 show a flow diagram illustrating the method of the present invention.

Although preferred embodiments of the invention are described for illustrative purposes, it should be understood that the invention may be embodied in other forms not specifically shown in the drawings. In particular, only a few of the instructional positions, maneuvers, and exercises according to the present invention are shown for illustrative purposes. Without limiting the invention, the terms positions, maneuvers, and exercises are used interchangeably, although each term also is used according to its ordinary meaning. The invention is not limited to the specific instruction discussed herein, but may also involve other positions, both yoga-based and non-yoga, that is effective in facilitating movement of fluid and solid matter along the digestive tract, ultimately leading to an induced defecation.

The present invention may be used for the examination of a bowel of a patient in need of such examination, which could be prescribed based on a patient exhibiting signs and symptoms associated with gastroparesis, gastroesophageal reflux disease, intestinal pseudo obstruction, or constipation, among other diseases, disorders, and conditions. The present invention may be used in connection with a treatment regimen for such things as gastrointestinal motility disorders, cyclical vomiting syndrome, obesity, improve digestion and general well-being by detoxification, irritable bowel syndrome, gas and bloating, and allergies.

Figures 1, 2:
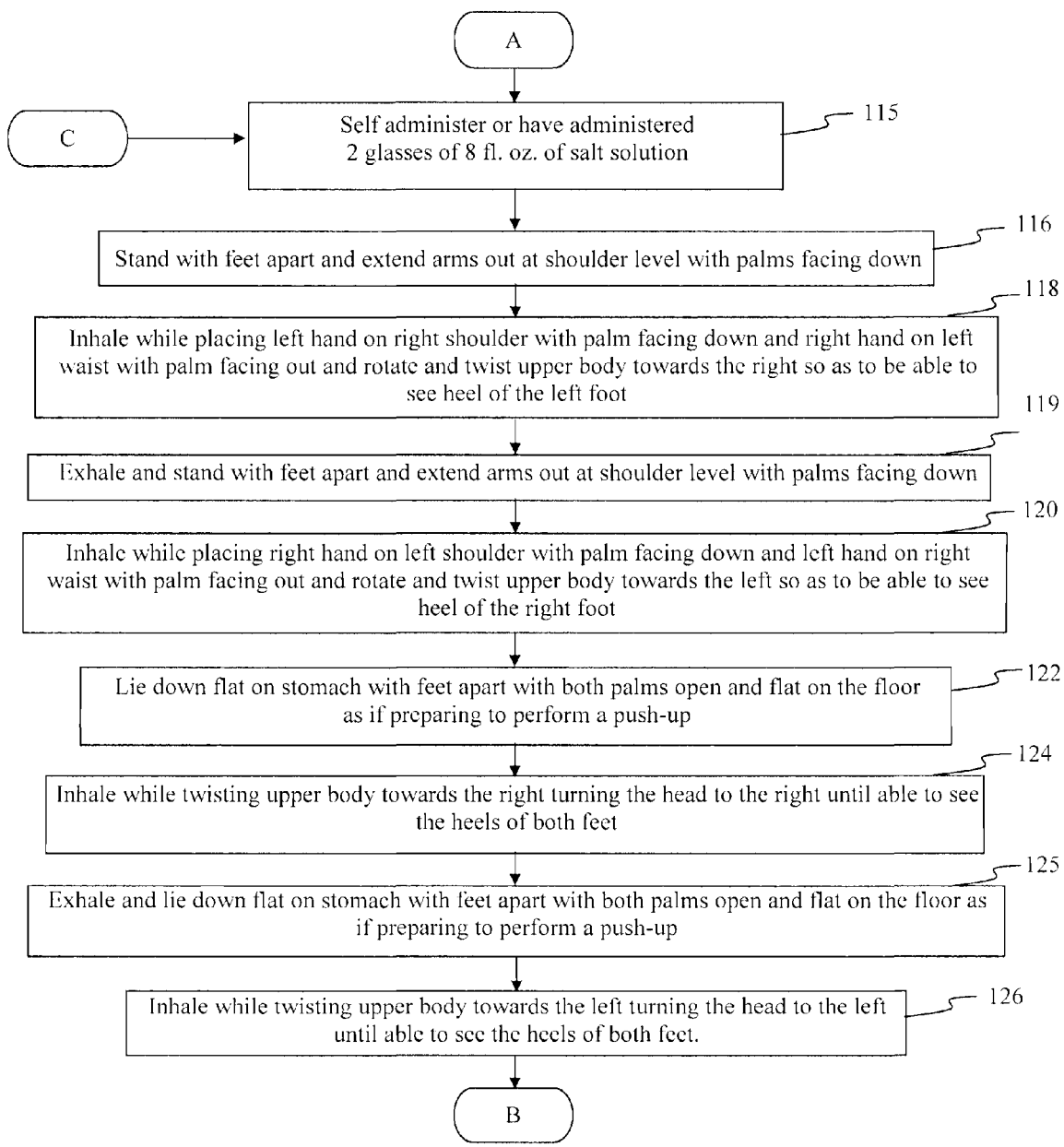
Figures 1, 2, 3:
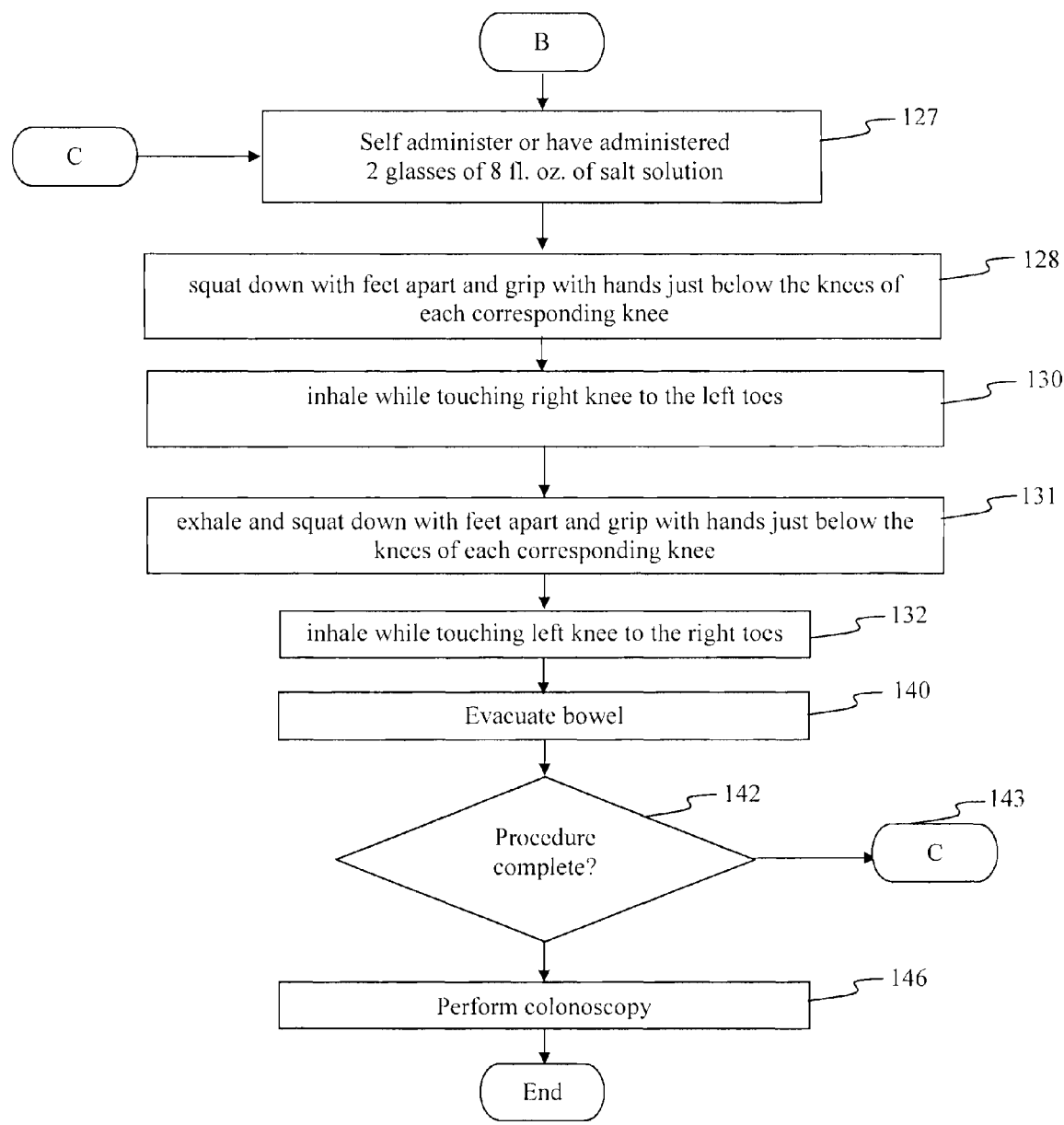

Referring to the flow chart in FIGS. 1-1, 1-2 and 1-3, a patient 102 is prescribed a colonoscopy for examination of his/her bowel. According to the present invention, the patient 102 receives or is provided an orally administrable solution (step 94). The solution should preferably have a concentration of 0.9% w/v (i.e. 9 gm/l; although a solution made from 15 to 20 g/l is also acceptable), and preferably should have a temperature of about 40 degrees C. A commercially available premixed normal saline solution suitable for consumption may be used, or the patient 102 may prepare the solution. The solution is preferably made from purified water, but tap water, spring water, and well water are also acceptable. The primary ingredient added to the water is sodium chloride, in any edible form. This includes table salt, iodized salt, edible rock salt, sea salt, and any other edible sodium chloride salt. One to five milliliters of lemon or lime juice may be added as flavor to the solution. Other flavorings may be added, including actual or synthetic flavorings of apple, pineapple, pomegranate, and many others, either alone or in combination with each other, to the specific preferred taste of the patient being administered the solution.

Two to 3 or even 4 liters of the solution may be needed to perform the present invention for a typical patient. Generally speaking, the average patient 102 can perform the invention and achieve a clear bowel movement with about 2 liters of the solution. Eighteen grams of sodium chloride should be completely dissolved in 2 liters of water. The mixing and dissolution of the sodium chloride may occur after the water is heated, or the saline mixture may be heated after the fact. Either way, it is preferable that the fully dissolved solution be heated to approximately 40 degrees C. at the time of practicing the invention, or at least initially when the solution is prepared.

Beginning at approximately 8 hours prior to practicing the invention, no solid or semi-solid substance should be consumed. Generally, between 5 and 8 hours prior to performing the invention, the patient 102 may drink at least 64 fl. oz. of clear liquids, but this is not a requirement. Examples of "clear liquids" include, but are not limited to, water, apple juice, white grape juice, Gatorade®, broth, hard candies, gelatin, and tea. And just prior to beginning practice of the invention, the patient 102 should prepare by relaxing, turning off all phones, beepers, and other communication devices for 3 to 4 hours prospectively. They should also remove all undergarments and wear only loosely fitting, comfortable clothing, making sure that the pants have an elastic waistband. The environment for practicing the invention should be quite and have a hard surface, and be near an available dedicated bathroom.

Once the solution has been prepared as described, or after a previously prepared solution is provided, the patient 102 is provided with an instruction to administer a portion of the solution and perform the steps of the invention in the manner described below. The patient 102 begins by drinking two 8 fl. oz. glasses of the prepared salt solution; emphasis on "drinking" continuously rather than "sipping" (step 98). While drinking two 8 fl. oz. glasses is ideal, drinking a lesser amount is also sufficient, depending on several factors, including the body mass of the patient 102, age, previous consumption of foods, medical conditions, and others. Moreover, while the patient 102 may consume the entire amount all at once, the patient 102 may also drink in increments, for example every 2 minutes, and/or between exercise instructions as described below.

Turning now to FIG. 1a, shown therein is a perspective view drawing of a patient 102 following a first exercise instruction 104 in the first set of exercises according to the present invention (step 100). In FIG. 1a, a patient 102 undergoing preparation for examination or treatment is instructed to begin in the "ready" position by standing erect with both feet together and both hands placed on top of the head with the palms facing up and the fingers of each hand interlocked with each other (step 104).

Turning now to FIG. 1b, shown therein is a perspective view drawing of a patient 102 following a second exercise instruction (step 106) in the first set of exercises according to the present invention. In FIG. 1b, the patient 102 is instructed to inhale while stretching the arms upward as much as possible from the position depicted in FIG. 1a and to stand on the toes of both feet.

Turning now to FIG. 1c, shown therein is a perspective view drawing of a patient 102 following a third exercise instruction (step 108) in the first set of exercises according to the present invention. In FIG. 1c, the patient 102 is instructed to exhale while returning to the "ready" position depicted in FIG. 1a. The three exercises depicted in FIGS. 1a through 1c represent the first set of exercises in the present invention and may be repeated several times, but preferably no more than about 10 times, before moving onto the second set of exercises.

Figure 2C:
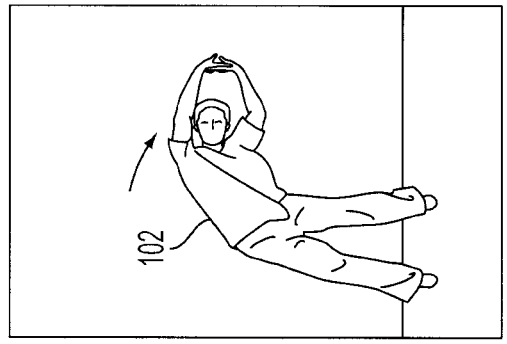
FIGS. 2a through 2c is perspective view drawings of a patient following a second series of instructions of a second set of exercises according to the present invention.
Figure 2B:
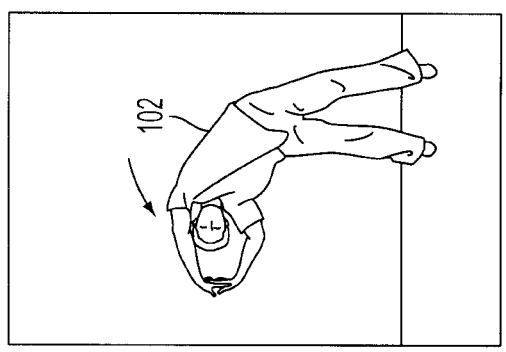
Figure 2A:
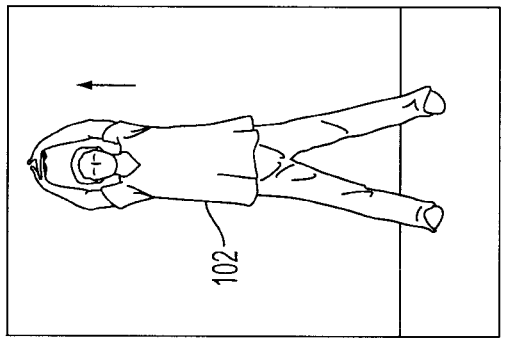

Turning now to FIG. 2a, shown therein is a perspective view drawing of a patient 102 following a first exercise instruction (step 110) in the second set of exercises according to the present invention. In FIG. 2a, the patient 102 is instructed to begin in the "ready" position by standing with the feet apart by about 1 to 2 feet, and the arms should be stretched straight upward with the palms facing up and both hands interlocked at the fingers.

Turning now to FIG. 2b, shown therein is a perspective view drawing of a patient 102 following a second exercise instruction (step 112) in the second set of exercises according to the present invention. In FIG. 2b, the patient 102 is instructed to inhale while bending at the waist to the right to an extent where the upper body forms an almost 90 degree angle with the right leg at the hip. The patient 102 is further instructed to maintain the outward stretched position of both arms while bending. Following this, the patient 102 is instructed to exhale while returning to the ready position (step 110) as depicted in FIG. 2a.

Turning now to FIG. 2c, shown therein is a perspective view drawing of a patient 102 following a third exercise instruction (step 113) in the second set of exercises according to the present invention. In FIG. 2c, the patient 102 is instructed to inhale while bending at the waist in a similar fashion as that depicted in FIG. 2b, except to the completely opposite, left side to an extent where the upper body forms an almost 90 degree angle with the left leg at the hip. The patient 102 is further instructed to maintain the outward stretched position of both arms while bending. The three exercises depicted in FIGS. 2a through 2c represent the second set of exercises in the present invention and may be repeated several times, but preferably no more than about 5 times, before moving onto the third set of exercises.

Upon completing the second set of exercise, the patient 102 is instructed to drink 2-eight oz. glasses of the prepared salt solution; emphasis on "drinking" continuously rather than "sipping" (step 115). As noted above, while drinking two 8 fl. oz. glasses is ideal, drinking a lesser amount is also sufficient. Moreover, as also mentioned above, while the patient 102 may consume the entire amount in one motion, the patient 102 may also drink in increments, for example every 2 minutes, between exercise instructions as described below.

Figure 3C:
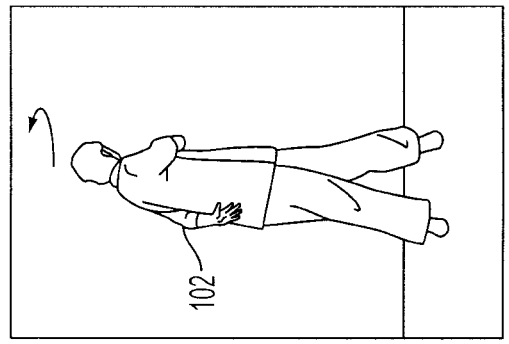
FIGS. 3a through 3c are perspective view drawings of a patient following a third series of instructions of a third set of exercises according to the present invention.
Figure 3B:
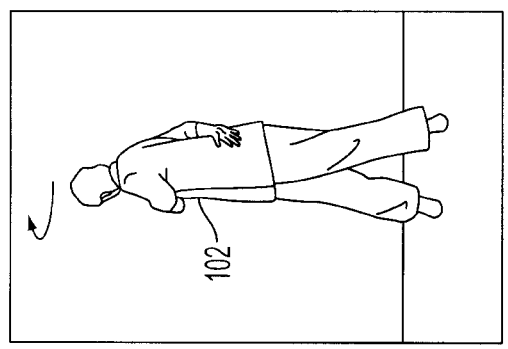
Figure 3A:
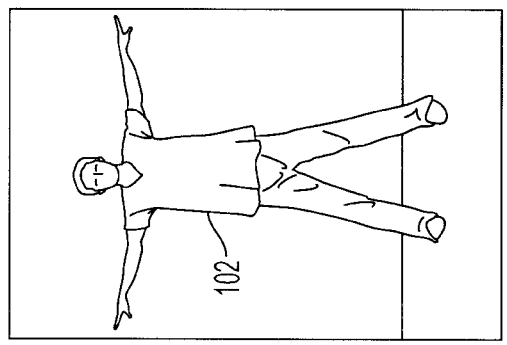

Turning now to FIG. 3a, shown therein is a perspective view drawing of a patient 102 following a first exercise instruction (step 116) in the third set of exercises according to the present invention. In FIG. 3a, the patient 102 is instructed to begin in the "ready" position by standing with the feet apart by 1 to 2 feet and the arms stretched outward at the shoulder level, perpendicular to the body and parallel to the floor, and having the palms facing down.

Turning now to FIG. 3b, shown therein is a perspective view drawing of a patient 102 following a second exercise instruction (step 118) in the third set of exercises according to the present invention. In FIG. 3b, the patient 102 is instructed to inhale while placing left hand on right shoulder with palm facing down, and right hand on left waist with palm facing out, and rotate and twist upper body towards the right so as to be able to see heel of the left foot. Following this, the patient 102 is further instructed to exhale and return to the ready position (step 119) as depicted in FIG. 3a.

Turning now to FIG. 3c, shown therein is a perspective view drawing of a patient 102 following a third exercise instruction (step 120) in the third set of exercises according to the present invention. In FIG. 3c, the patient 102 is instructed to inhale while placing right hand on left shoulder with palm facing down, and left hand on right waist with palm facing out and rotate and twist upper body towards the left so as to be able to see heel of the right foot. The three exercises depicted in FIGS. 3a through 3c represent the third set of exercises in the present invention and may be repeated several times, but preferably no more than about 5 times, before moving onto the fourth set of exercises.

Figure 4C:
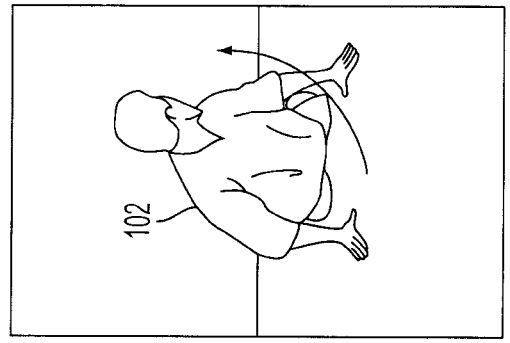
FIGS. 4a through 4c are perspective view drawings of a patient following a fourth series of instructions of a fourth set of exercises according to the present invention.
Figure 4B:
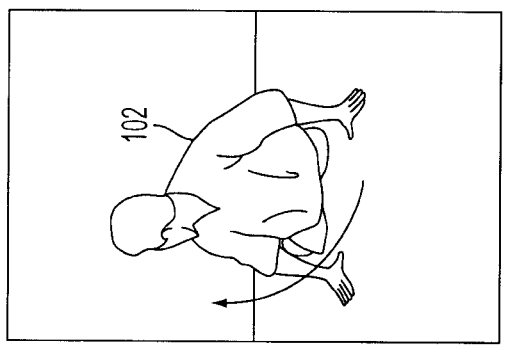
Figure 4A:
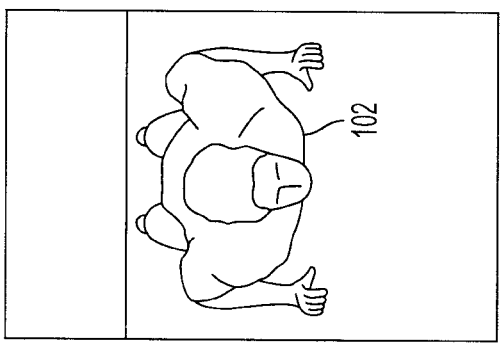

Turning now to FIG. 4a, shown therein is a perspective view drawing of a patient 102 following a first exercise instruction (step 122) in the fourth set of exercises according to the present invention. In FIG. 4a, the patient 102 is instructed to begin in the "ready" position by lying down flat on stomach with feet apart and with both palms open and flat on the floor as if preparing to perform a push-up.

Turning now to FIG. 4b, shown therein is a perspective view drawing of a patient 102 following a second exercise instruction (step 124) in the fourth set of exercises according to the present invention. In FIG. 4b, the patient 102 is instructed to inhale while twisting upper body toward the right turning the head to the right until able to see the heels of both feet. Ideally, a patient should twist up to a 90-degree angle, however a greater than or less attempt would be sufficient. Following this, the patient 102 is further instructed to exhale while returning the body to the ready position (step 125) as depicted in FIG.

Turning now to FIG. 4c, shown therein is a perspective view drawing of a patient 102 following a third exercise instruction (step 126) in the fourth set of exercises according to the present invention. In FIG. 4c, the patient 102 is instructed to inhale while twisting upper body towards the left turning the head to the left until able to see the heels of both feet. The three exercises depicted in FIGS. 4a through 4c represent the fourth set of exercises in the present invention and may be repeated several times, but preferably no more than about 5 times, before moving onto the fifth set of exercises.

Upon completing the fourth set of exercise, the patient 102 is instructed to drink 2-eight oz. glasses of the prepared salt solution; emphasis on "drinking" continuously rather than "sipping" (step 127). Again, while drinking two 8 fl. oz. glasses is ideal, drinking a lesser amount is also sufficient. Moreover, as noted above, while the patient 102 may consume entire amount in one motion, the patient 102 may also drink in increments, for example every 2 minutes, between exercise instructions.

Figure 5C:
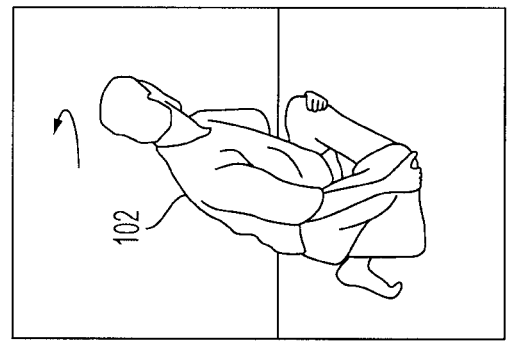
FIGS. 5a through 5c are perspective view drawings of a patient following a fifth series of instructions of a fifth set of exercises according to the present invention.
Figure 5B:
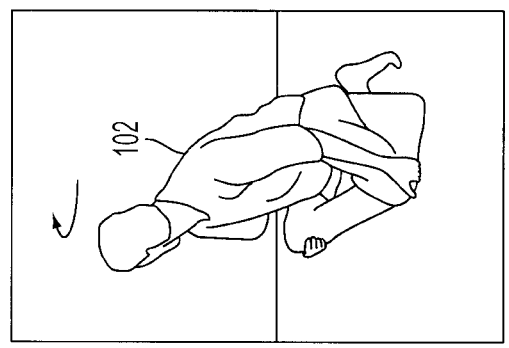
Figure 5A:
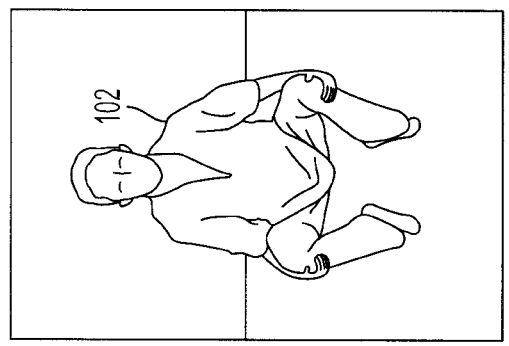

Turning now to FIG. 5a, shown therein is a perspective view drawing of a patient 102 following a first exercise instruction (step 128) in the fifth set of exercises according to the present invention. In FIG. 5a, the patient 102 is instructed to begin in the "ready" position by squatting down with feet apart and griping with both hands just below the knees of each corresponding leg.

Turning now to FIG. 5b, shown therein is a perspective view drawing of a patient 102 following a second exercise instruction (step 130) in the fifth set of exercises according to the present invention. In FIG. 5b, the patient 102 is instructed to inhale while touching the right knee to the left toes. The patient 102 is further instructed to exhale while returning to the ready position (step 131) as depicted in FIG. 5a.

Turning now to FIG. 5c, shown therein is a perspective view drawing of a patient 102 following a third exercise instruction (step 132) in the fifth set of exercises according to the present invention. In FIG. 5c, the patient 102 is instructed to inhale while touching the left knee to the right toes. The three exercises depicted in FIGS. 5a through 5c represent the fifth set of exercises in the present invention and may be repeated several times, but preferably no more than about 5 times.

The patient 102 is instructed, if at any point when practicing the invention an urge to defecate arises, to proceed to the toilet and commence passing the stool (step 140), but patient 102 should not strain. Although step 140 is shown at the end of the last exercise, it may be performed at any time. After step 140, the patient 102 should evaluate, with our without assistance from the patient's healthcare provider, whether a clear, liquid bowel movement has been achieved (step 142). The patient 102 is further instructed to perform the above sequence of exercises as shown in FIGS. 1a through 5c as necessary until a clear, liquid bowel movement is achieved (step 143). New batches of lukewarm liquid around 40 degrees C. may need to be prepared for each new cycle of the exercise sequence, if necessary. Approximately 2 to 3 liters of the solution and 2 to 3 repetitions of the complete sequence of exercises shown in FIGS. 1a through 5c are expected for a typical patient to complete the process sufficient to perform a colonoscopy (step 146).

Following the performance of the steps as detailed above, the patient 102 is instructed to not eat any solid or semi-solid foods, and to limit consumption to water only until the completion of the scheduled colonoscopy procedure for early the next morning or shortly after completion of the exercises described above. No consumption of substances 3 hours prior to colonoscopy is recommended.

Once the above sequence of steps is performed, or at least a portion of the steps are performed by a patient 102 following the instructions provided, the patient 102 is further prepared for the actual colonoscopy examination according to and following well known clinical or hospital procedures, including those involving anesthesiology, patient monitoring, and the actual examination itself (step 146).

The efficacy and safety of the present invention was investigated in 42 patients between the ages of 18 and 65 in a clinical study. The patient population was split into two groups: Group A was the study group, which consisted of 21 individuals who practiced the invention, and Group B was the control group, which consisted of 21 individuals who drank Nulytely®, a prescription bowel preparation product. All patients were scheduled to undergo colonoscopy the following day, but Group A had colonoscopies on the same day. Group A patients were asked to perform a defined set of light yoga exercises according to the methods described herein, alternating with drinking lukewarm salt water (40 C) prepared by dissolving eighteen (18) grams of sodium chloride (NaCl) in two (2) liters of water. Patients in Group B drank Nulytely as per the manufacturer's instructions and then presented for colonoscopy the next day.

Subsequently, the colonoscopies were performed on the patient population by a single gastroenterologist. The individual patient colonoscopy preparation was rated on a four point grading scale: poor prep (value 1), sub-optimum (value 2), optimum (value 3), and excellent (value 4). The results revealed that 14 out of the 21 patients in Group A, and 10 out of the 21 patients in Group B, achieved excellent preparation. Four out of the 21 patients in Group A, and 9 out of the 21 patients in Group B, achieved optimum preparation. One patient out of each group achieved sub-optimum preparation. Two patients in Group A, and 1 patient in Group B, achieved poor preparation.

Upon statistical analysis, the grading score means were found to be 3.43 and 3.34 in Groups A and B, respectively. These findings, however, were not statistically significant (p-value >0.05). The results showed that the group using the preparation technique disclosed in the present invention demonstrated a slight statistically non-significant improvement over NuLytely, thus suggesting the two groups to be equal in efficacy. However, the present preparation method demonstrated a statistically significant (p-value <0.05) superiority over the national colonoscopic success rates, which is at 85%. The statistical test used was the "t test." The study investigators found that using a lukewarm saline solution and combining it with an exercise routine as described herein is a safe, simple, and cost effective method for achieving proper bowel preparation to undergo a colonoscopy examination by endoscope.

Although certain presently preferred embodiments of the disclosed invention have been specifically described herein, it will be apparent to those skilled in the art to which the invention pertains that variations and modifications of the various embodiments shown and described herein may be made without departing from the spirit and scope of the invention. For example, other bending and twisting maneuvers or exercises similar to those described above and shown in the drawings may be used successfully in cleansing the bowel. Likewise, exercises not similar to those described above, such as walking on a treadmill at a steady speed of at least about 5 mph, or brisk walking, and use of step stool exercises, also are believed to provide successful outcomes in cleansing the bowel. The specific sequence of the exercises is important but not critical to the efficacy of the technique for purposes of colonoscopy and/or treatment. Accordingly, it is intended that the invention be limited only to the extent required by the appended claims, prior art, and applicable rules of law.

I claim:

1. A method of cleansing a patient's colon in need of examination, comprising:
    administering to the patient a treatment regimen intended to cleanse the patient's colon, wherein the treatment regimen effectively prepares the patient's colon to undergo the examination by one of colonoscopic, endoscopic, and sigmoidoscopic instruments for the identification of colon-related diseases or disorders, wherein the treatment regimen comprises administering to the patient a first predetermined quantity of an oral cleansing solution all at once; performing by the patient a first exercise; administering to the patient a second predetermined quantity of the solution all at once; performing by the patient a second exercise; administering to the patient a third predetermined quantity of the solution all at once; performing by the patient a third exercise; administering to the patient a fourth predetermined quantity of the solution all at once; performing by the patient a fourth exercise; administering to the patient a fifth predetermined quantity of the solution all at once; and performing by the patient a fifth exercise, wherein the solution comprises sodium chloride mixed with a diluent and optionally a flavorant to produce a solution comprising from about 15 to about 20 grams of sodium chloride per 2 liters of the diluent, wherein each of the predetermined quantities of the oral cleansing solution total at least about 8-16 ounces, and wherein performing the first exercise step comprises, with reference to the patient's body: following a first instruction by the patient to stand erect with both feet together with interlocking fingers and hands on top of the head with palms facing up, following a second instruction by the patient to inhale while stretching arms upwards as much as possible and standing on toes, and following a third instruction by the patient to exhale and stand erect with both feet together with interlocking fingers and hands on top of the head with palms facing up; performing the second exercise step comprises, with reference to the patient's body: following a fourth instruction by the patient to stand with feet apart with interlocking fingers and arms stretched upwards above the head, following a fifth instruction by the patient to inhale while bending at the waist and tilt outstretched arms to the right, following a sixth instruction by the patient to exhale and stand with feet apart with interlocking fingers and arms stretched upwards above the head, and following a seventh instruction by the patient to inhale while bending at the waist and tilt outstretched arms to the left; performing the third exercise step comprises, with reference to the patient's body: following an eighth instruction by the patient to stand with feet apart and extend arms out at shoulder level with palms facing down, following a ninth instruction by the patient to inhale while placing left hand on right shoulder with palm lacing down and right hand on left waist with palm facing out and rotate and twist upper body towards the right so as to be able to see heel of the left foot, following a tenth instruction by the patient to exhale and stand with feet apart and extend arms out at shoulder level with palms facing down, and following an eleventh instruction by the patient to inhale while placing right hand on left shoulder with palm facing down and left hand on right waist with palm facing out and rotate and twist upper body towards the left so as to be able to see heel of the right foot; performing the fourth exercise step comprises, with reference to the patient's body: following a twelfth instruction by the patient to lie down flat on stomach with feet apart with both palms open and flat on the floor as if preparing to perform a push-up, following a thirteenth instruction by the patient to inhale while twisting upper body towards the right turning the head to the right until able to see the heels of both feet, following a fourteenth instruction by the patient to exhale and lie down flat on stomach with feet apart with both palms open and flat on the floor as if preparing to perform a push-up, and following a fifteenth instruction by the patient to inhale while twisting upper body towards the left turning the head to the left until able to see the heels of both feet; performing the fifth exercise step comprises, with reference to the patient's body: following a sixteenth instruction by the patient to squat down with feet apart and grip with hands just below the knees of each corresponding knee, following a seventeenth instruction by the patient to inhale while touching right knee to the left toes, following a eighteenth instruction by the patient to exhale and squat down with feet apart and grip with hands just below the knees of each corresponding knee, and following a nineteenth instruction by the patient to inhale while touching left knee to the right toes.

2. The method according to claim 1, wherein the step of administering to the patient the first predetermined quantity of the solution occurs at a first predetermined time period; and the step of performing by the patient the first exercise occurs at a second predetermined time period that is different than the first time period.

3. The method according to claim 1, further comprising the step of performing a colonoscopic examination of the patient within about 24 hours of the first and second time periods.

4. The method according to claim 1, wherein the solution comprises a concentration made from 18 grams of sodium chloride per 2 liters of water.

5. The method according to claim 1, wherein the solution is maintained at about 40 C.

6. The method according to claim 1, wherein said colon-related diseases or disorders include one of gastrointestinal motility disease, cyclical vomiting syndrome, obesity, improve digestion and general well being by detoxification, irritable bowel syndrome, gas and bloating, and allergies.

7. A method for preparing a patient in need of colonoscopic examination by endoscope or other means, comprising the steps of:

providing to the patient a first predetermined quantity of a salt solution for oral consumption at a first predetermined time period, wherein the solution comprises sodium chloride, a flavorant, and a diluent to produce a solution comprising from about 15 to about 20 grams of sodium chloride per 2 liters of diluent;

instructing the patient to perform at least five different exercises in sequential order after the first predetermined time period, wherein approximately eight fluid ounces of the solution are orally administered to the patient all at once before the performance of each of the exercises, and wherein the administering and performing steps are intended to facilitate production of fecal material from the patient's colon and effectively cleanse the colon to permit examination by one of colonoscopic, endoscopic, and sigmoidoscopic instruments for identification of colon-related diseases or disorders; and conducting the colonoscopic examination of the patient after the at least five exercises have been performed; wherein performing a first exercise step comprises, with reference to the patient's body: following a first instruction by the patient to stand erect with both feet together with interlocking fingers and hands on top of the head with palms facing up, following a second instruction by the patient to inhale while stretching arms upwards as much as possible and standing on toes, and following a third instruction by the patient to exhale and stand erect with both feet together with interlocking fingers and hands on top of the head with palms facing up; performing a second exercise step comprises, with reference to the patient's body: following a fourth instruction by the patient to stand with feet apart with interlocking fingers and arms stretched upwards above the head, following a fifth instruction by the patient to inhale while bending at the waist and tilt outstretched arms to the right, following a sixth instruction by the patient to exhale and stand with feet apart with interlocking fingers and arms stretched upwards above the head, and following a seventh instruction by the patient to inhale while bending at the waist and tilt outstretched arms to the left; performing a third exercise step comprises, with reference to the patient's body: following an eighth instruction by the patient to stand with feet apart and extend arms out at shoulder level with palms facing down, following a ninth instruction by the patient to inhale while placing left hand on right shoulder with palm lacing down and right hand on left waist with palm facing out and rotate and twist upper body towards the right so as to be able to see heel of the left foot, following a tenth instruction by the patient to exhale and stand with feet apart and extend arms out at shoulder level with palms facing down, and following an eleventh instruction by the patient to inhale while placing right hand on left shoulder with palm facing down and left hand on right waist with palm facing out and rotate and twist upper body towards the left so as to be able to see heel of the right foot; performing a fourth exercise step comprises, with reference to the patient's body: following a twelfth instruction by the patient to lie down flat on stomach with feet apart with both palms open and flat on the floor as if preparing to perform a push-up, following a thirteenth instruction by the patient to inhale while twisting upper body towards the right turning the head to the right until able to see the heels of both feet, following a fourteenth instruction by the patient to exhale and lie down flat on stomach with feet apart with both palms open and flat on the floor as if preparing to perform a push-up, and following a fifteenth instruction by the patient to inhale while twisting upper body towards the left turning the head to the left until able to see the heels of both feet; performing a fifth exercise step comprises, with reference to the patient's body: following a sixteenth instruction by the patient to squat down with feet apart and grip with hands just below the knees of each corresponding knee, following a seventeenth instruction by the patient to inhale while touching right knee to the left toes, following a eighteenth instruction by the patient to exhale and squat down with feet apart and grip with hands just below the knees of each corresponding knee, and following a nineteenth instruction by the patient to inhale while touching left knee to the right toes.

8. The method according to claim 7, wherein the solution comprises 18 grams of sodium chloride per 2 liters of water.

9. The method according to claim 7, wherein the solution is maintained at about 40 C.

* * * * *